United States Patent
Toedtli

[11] Patent Number: 5,295,401
[45] Date of Patent: Mar. 22, 1994

[54] TEXTILE ON-LINE SAMPLING INSPECTION

[75] Inventor: Sergej Toedtli, Wollerau, Switzerland

[73] Assignee: Siegfried Peyer AG, Wollerau, Switzerland

[21] Appl. No.: 784,406

[22] PCT Filed: Apr. 22, 1991

[86] PCT No.: PCT/CH91/00093
§ 371 Date: Dec. 20, 1991
§ 102(e) Date: Dec. 20, 1991

[87] PCT Pub. No.: WO91/16625
PCT Pub. Date: Oct. 31, 1991

[30] Foreign Application Priority Data

Apr. 26, 1990 [CH] Switzerland ............. 1436/90-5

[51] Int. Cl.$^5$ ............................................. G01N 33/36
[52] U.S. Cl. ......................... 73/863.92; 73/160; 73/159; 356/429
[58] Field of Search .......... 73/159, 160, 863.92, 73/863.91; 28/187, 188, 189, 225, 227; 340/675, 677; 356/429, 430, 431

[56] References Cited

U.S. PATENT DOCUMENTS

| | | | |
|---|---|---|---|
| 3,333,467 | 8/1967 | Hoskins | 73/160 |
| 3,377,852 | 4/1968 | Leistra | 73/160 |
| 3,669,552 | 6/1972 | Briscoe | 73/159 X |
| 3,795,906 | 3/1974 | Erbstein | 340/677 X |
| 4,058,962 | 11/1977 | Spescha et al. | 73/160 X |
| 4,295,252 | 10/1981 | Robinson et al. | 73/160 X |
| 4,791,812 | 12/1988 | Kirby et al. | 73/160 |
| 4,827,781 | 5/1989 | Völlm | 73/864.41 |

FOREIGN PATENT DOCUMENTS

| | | | |
|---|---|---|---|
| 0247420 | 12/1987 | European Pat. Off. | |
| 1124268 | 2/1962 | Fed. Rep. of Germany | 73/160 |
| 2137564 | 3/1972 | Fed. Rep. of Germany | 73/160 |
| 230490 | 3/1969 | U.S.S.R. | 73/160 |
| 1315958 | 5/1973 | United Kingdom | |

Primary Examiner—Tom Noland
Attorney, Agent, or Firm—Walter C. Farley

[57] ABSTRACT

A process is disclosed for sampling textile fiber skeins. A fiber skein (2) continuously moved in the longitudinal direction (23) is intermittently brought to a stop within a defined section (4, 28). The profile of the immobilized section (4, 28) of the fiber skein (2) is flattened at least in partial region (24) and the textile analysis is carried out on this temporarily immobilized, flattened partial region (24) of the fiber skein.

16 Claims, 2 Drawing Sheets

TEXTILE ON-LINE SAMPLING INSPECTION

FIELD OF THE INVENTION

The invention relates to a method for the random-sample analysis of textile fiber strands.

BACKGROUND OF THE INVENTION

In the sense of the method of the invention, the term "fiber strands" is used to include both ordered and irregular strands of textile single fibers (slivers) and furthermore also webs.

It is known in the textile industry to use mechanical or capacitive sensors to monitor automatically mass fluctuations of continuously moving fiber strands or slivers for purposes of quality control. On the other hand, foreign particles and foreign fibers are measured manually by a lab technician who randomly pulls apart slivers on a luminous table and visually searches for foreign particles and counts them. The properties of the individual fibers cannot be measured at all, and therefore it is impossible to ascertain changes in parameters (for instance length, crimping) caused by processing conditions.

SUMMARY OF THE INVENTION

An object of the invention is improvement of the methods. It is the object of the invention to create a method for the random sampling of textile strands allowing non-destructive analysis of the moving fiber strand.

Essentially the advantages of the invention are that by means of its method, it is possible to carry out "on-line" analysis by randomly sampling the moving fiber strand (for instance a card sliver) without residually damaging the fiber strand.

Further advantages are automated analysis of foreign particles and detecting changes in length due to processing conditions. These values also may be used to optimize the previous processing. The routinely occurring doubling of the slivers arising in such processing may be monitored and controlled, so that the values of the fiber parameters, and thereby also yarn quality, remain constant.

BRIEF DESCRIPTION OF THE DRAWINGS

An illustrative implementation of the invention which at the same time elucidates the principle of operation is shown in the drawings and described comprehensively below. In the drawings, FIG. 1 schematically shows apparatus with which to carry out the method of the invention, FIG. 2 schematically shows the means of the invention in the apparatus of FIG. 1 for flattening the fiber strands prior to its actuation, FIG. 3 schematically shows the means of the invention of the apparatus of FIG. 1 for flattening the fiber strands after a sliver has been seized.

DESCRIPTION OF THE PREFERRED EMBODIMENTS

Figure 1:
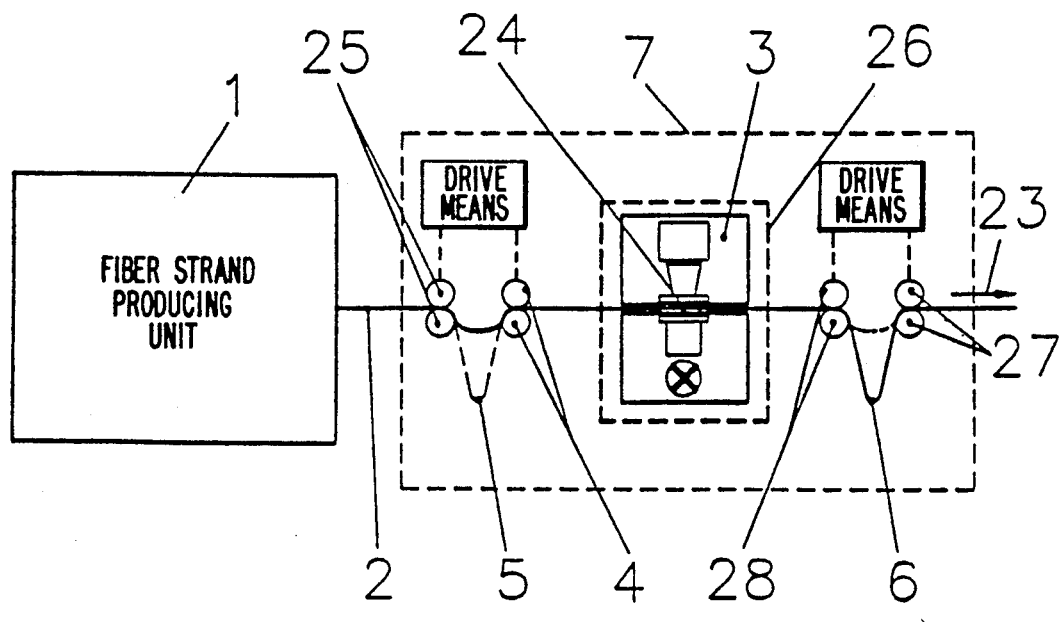

The measurement instrumentation 7 shown in FIG. 1 used to carry out the method of the invention essentially comprises fiber transporting means 25, 4, 28, 27, fiber strand retaining or damming means 5,6, fiber strand leveling means 3; and a textile measuring apparatus 26. The instrumentation 7 can be connected directly, on-line to the output of a unit 1 producing a fiber strand or sliver 2 such as a stretching device, a card or a combing means.

The fiber strand 2 entering the measurement instrumentation 7 on the left at a speed between 8 and 120 m/min passes between two pairs of cooperating rolls 25, 25; 4,4 and arrives in the region of the textile measuring apparatus 26 and finally, after passing between two cooperating pairs of rolls 28, 28; 27, 27 mounted a distance of 0.1 to 1.0 m apart, leaves the measurement instrumentation 7 in the longitudinal direction 23. Preferably the material, surface, size and drive and control by electric motor of the pairs of rolls corresponds to those of standard stretching equipment.

By briefly stopping the pairs of rolls 4 and 28 while the pairs of rolls 25 and 27 keep on rotating, the fiber strand 2 within the segment bounded by the pairs of rolls 4 and 28 can be stopped for a time, the fiber strand 2 being briefly retained in the retaining space 5 (between the pairs of rolls 25 and 4) and the accumulation formed in the previous rest phase in the retaining space 6 being levelled.

Figures 2, 3:
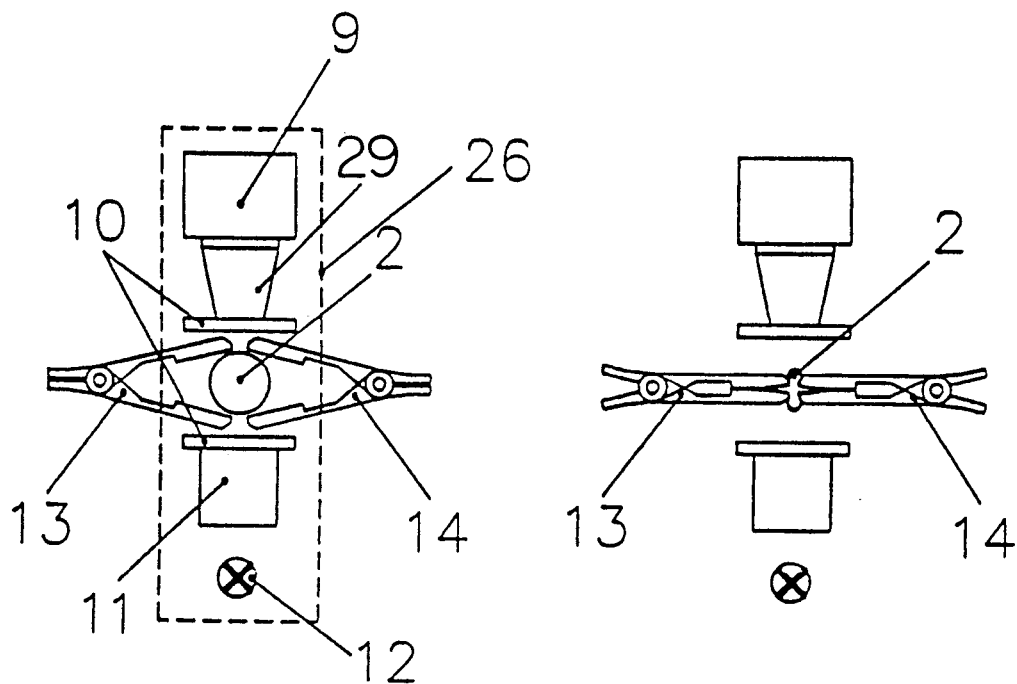

Between the two retaining spaces 5 and 6, the path of the fiber strand 2 passes between means 3 for levelling this fiber strand which is represented in FIG. 2 by the plates 10 of an optical fiber-measuring system 26. The mutually displaceable plates 10 permit short-term compression of the fiber strand 2 in a zone 24 of the defined segment 4, 28 which is at rest, this compression being synchronized with the retaining phases of the fiber strand 2 in the retaining spaces 5 and 6. The contour of the fiber strand 2 is levelled or flattened to such an extent that it is amenable to discontinuous, textile checking, for instance in an optical manner, by means of the textile measuring system 26. Preferably the flattening of the fiber-strand contour 2 results in arranging the individual fibers in a single layer.

Preferably the textile measuring system 26 is based on image-data processing and is schematically shown in FIG. 2 as including a light source 12, illuminating optics 11, imaging optics 29 and a camera 9. Details of this measuring system 26 are described in the Swiss patent 679,428 which corresponds to U.S. Ser. No. 07/768,618, filed Oct. 1, 1991.

However, other measuring systems 26 also may be used, for instance employing different optics, with integrating measurements or with reflected light measurements.

Once the textile parameters have been measured by means of the measuring apparatus 26, the temporarily flattened zone 24 of the fiber strand 2 is released and the segment of the fiber strand 2 that was bounded by the pairs of rolls 4 and 28 is conveyed further by the renewed rotation of the pairs of rolls 4 and 28, the briefly deformed zone 24 being able to regenerate so that, in sum, the fiber strand 2 does not undergo any permanent damage due to measurement.

Figure 4:
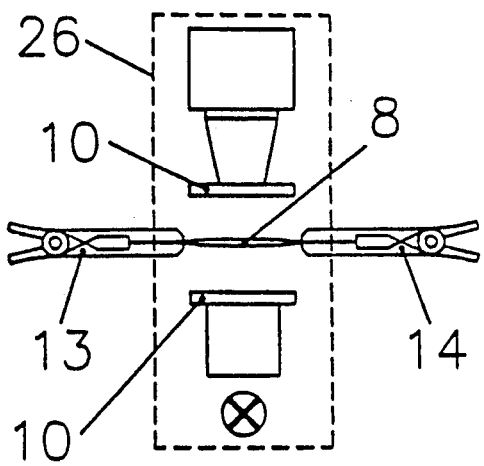
FIG. 4 schematically shows the fiber-strand flattening means of the equipment of the invention of FIG. 1 after the sliver has been drawn apart.

Aside from the procedure described in relation to FIG. 1, the fiber-strand contour 2 also may be flattened using a special device such as shown in FIGS. 2–4. As shown in FIG. 3, the fiber strand 2 is seized while being at rest within the zone of the textile-measuring apparatus 26 by a pair of tongs 13, 14 and is clamped as shown in FIG. 4, and is flattened by pulling apart the pair of tongs 13, 14 to form a transparent and preferably single-layer web 8.

Figure 5:
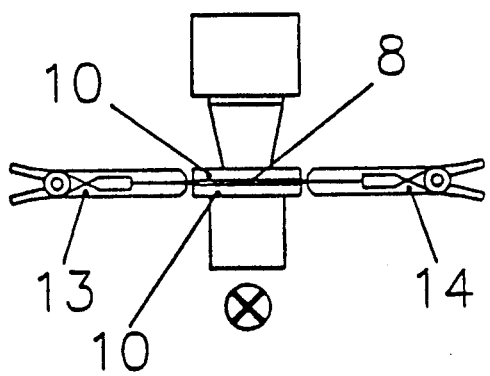
FIG. 5 is a variation of the detailed FIG. 4 at the time of measurement.

FIGS. 4 and 5 show furthermore how a transparent cotton web 8 while being at rest in the zone of the textile measuring system 26 is seized at its edges by the lateral pair of tongs 13, 14 and is further flattened by tension so as to create a single-layer web. Simultaneously the annular plates 10 of the illuminating optics 11 and imaging optics 9 of the textile measuring system 26 are forced against each other, whereby the web 8, which is clamped and drawn apart by the pair of tongs 13, 14, is flattened further, so that the optical textile check based on image-data processing, which presumes a thin, planar arrangement of the fiber material to be analyzed, can be carried out.

Figure 6:
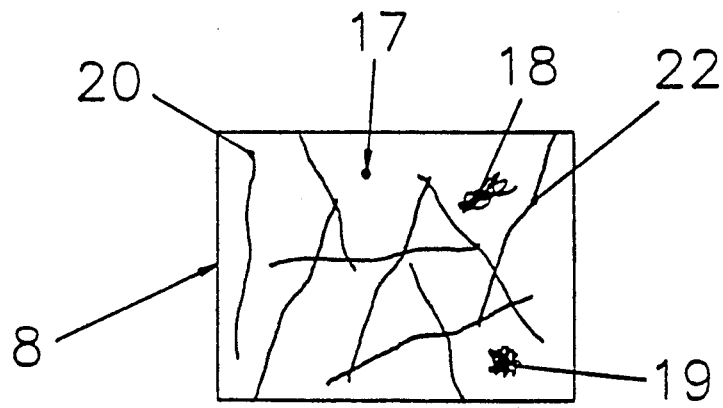
FIG. 6 shows typical interfering particles in a cotton web which can be analyzed by the method of the invention.

FIG. 6 shows an image window of the kind generated by the imaging optics 9 of the textile measuring system 26 based on image-data processing; it displays typical interfering particles in a cotton fiber web, illustratively soil 17, neps 18, seed-coat fragments 19, fiber ends 20 and fibers 22, which can be analyzed by the method of the invention. The methodology of recognizing such interfering particles and for determining the relative and absolute proportion of the diverse interfering particles is known and is described, for example, in MELLIAND TEXTILBERICHTE 12/1989, pp 887–9.

Figure 7:
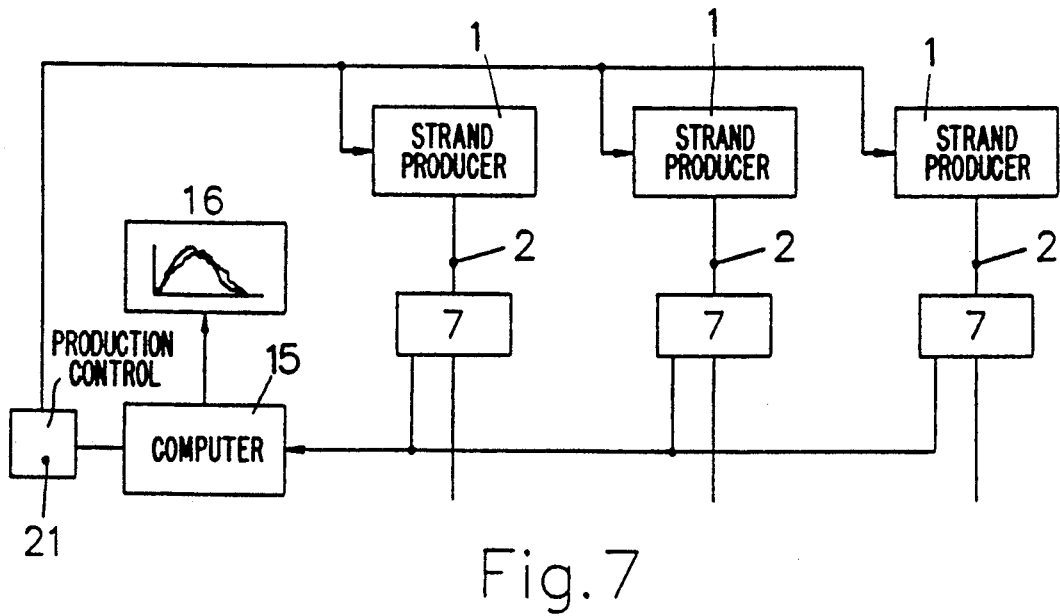
FIG. 7 shows a plurality of centrally controlled apparatus in accordance with the invention to simultaneously and randomly analyze several textile fiber strands employing different analyses.

FIG. 7 shows a plurality of means 1 producing a fiber strand, each with a measurement instrumentation 7 of the invention that is controlled by a single, central computer 15.

The sliver parameters change relative slowly even if, based on the measurement test results, a change was carried out in the means 1 producing the fiber strand 2. The measurement technique is substantially faster. Therefore several slivers can be simultaneously monitored by a computer 15. An alarm may be sounded for substantial discrepancies. Further optimization may be carried out by the issuing suggestions for doubling the slivers of different quality or undertaking such directly.

The data recorded by the computer, 15 may be graphically or otherwise shown on a display 16 and can be used by means of an interface 21 to control the fiber-strand producing units 1.

The frequency of fiber-ends in the image window indicates fiber length. If this fiber length is less than in the initial material, then the means 1 producing a fiber strand 2 must be the cause. This information may be communicated through the interface 21 to the corresponding equipment 1 which then corrects its parameters until fiber damage is optimally minimized. The computer 15 passes this information to the corresponding machines 1. Further possibilities of this sort are described in the Swiss patent 678,230, VERFAHREN ZUR FREQUENZANALYSE AN BEWEGTEN FASERKOLLEKTIVEN ("Frequency analysis of moving fiber sets") which corresponds to U.S. Ser. No. 07/634,213, filed Feb. 6, 1991 and abandoned as file wrapper continuing application Ser. No. 07/931,894 on Aug. 18, 1992, which is itself now abandoned.

I claim:

1. A method for non-destructively analyzing samples of a textile fiber strand comprising the steps of
    continuously moving an elongated fiber strand longitudinally to a testing location;
    temporarily stopping a selected segment of the strand at the testing location;
    flattening the selected segment while it is stopped;
    analyzing the flattened segment while it is stopped; and
    resuming the longitudinal motion of the selected segment.

2. A method according to claim 1 wherein the flattening includes forming the strand into a single-layer web.

3. A method according to claim 2 wherein the strand is moved at a continuous longitudinal speed of between 8 and 120 meters per minute.

4. A method according to claim 3 wherein the steps of temporarily stopping, flattening and analyzing are repetitively performed at longitudinal spaced segments of the strand at a rate of between 2 and 60 times per minute.

5. A method according to claim 1 wherein the strand is moved at a continuous longitudinal speed of between 8 and 120 meters per minute.

6. A method according to claim 1 wherein the steps of temporarily stopping, flattening and analyzing are repetitively performed at longitudinally spaced segments of the strand at a rate of between 2 and 60 times per minute.

7. An apparatus for non-destructively analyzing samples of a textile fiber strand without removing the samples from the strand comprising the combination of
    means for longitudinally delivering a continuously moving textile fiber strand to a testing location, for longitudinally removing tested strand from the testing location, and for temporarily stopping a segment of said strand at the testing location while accumulating slack in said strand at a delivery side of said testing location;
    means at said testing location for flattening said segment of said strand; and
    means at said testing location for analyzing said segment while said segment is stopped and flattened.

8. An apparatus according to claim 7 wherein said means for delivering, removing and stopping includes
    first and second pairs of rolls rotatably mounted at said delivery side of said testing location and engaging said strand,
    third and fourth pairs of rolls rotatably mounted at an output side of said testing location and engaging said strand, and
    electric motor drive means for controllably driving said rolls to thereby temporarily stop said selected segment.

9. An apparatus according to claim 8 wherein said first and second pairs of rolls are spaced apart by a distance of between about 0.1 meter and 1.0 meter to form a retaining space for a slack portion of said fiber strand.

10. An apparatus according to claim 9 wherein said third and fourth pairs of rolls are spaced apart by a distance of between about 0.1 and 1.0 meter to form a second retaining space for a slack portion of said fiber strand.

11. An apparatus according to claim 10 wherein said means for analyzing includes optical analyzing means and means for flattening comprising first and second parallel plates on opposite sides of a path for said strand, said plates being relatively movable to flatten said strand therebetween.

12. An apparatus according to claim 10 wherein said means for flattening includes a pair of tongs mounted laterally on opposite sides of a path for said fiber strand, said tongs being movable to engage and flatten said strand.

13. An apparatus for non-destructively analyzing samples of a plurality of textile fiber strands from a plurality of sources of strands without removing the samples from the strands comprising the combination of a plurality of means for longitudinally delivering a plurality of continuously moving textile fiber strands to individually testing locations, for longitudinally removing tested strands from the testing location, and for temporarily stopping segments of said strands at the testing locations while accumulating slack in said strands at a delivery side of said testing locations;

means at each said testing location for flattening said segment of a strand delivered thereto;

means at each said testing location for analyzing said segment while said segment is stopped and flattened; and a central computer connected to control each said means for delivering, removing and stopping and for controlling each said means for analyzing.

14. An apparatus according to claim 13 wherein said central computer records data from said means for analyzing, said apparatus further comprising means for displaying said data.

15. An apparatus according to claim 14 wherein said data are displayed graphically.

16. An apparatus according to claim 15 and further comprising an interface unit connected between said computer and said sources for controlling said sources in response to recorded data.

* * * * *